United States Patent
Lauk (10) Patent No.: US 10,743,793 B2
(45) Date of Patent: Aug. 18, 2020

(54) SYSTEMS AND METHODS FOR DELIVERING AN AGENT TO A USER'S LUNGS AND FOR SIMULTANEOUSLY MONITORING LUNG HEALTH

(71) Applicant: RESPEQ INC., Baltimore, MD (US)

(72) Inventor: Michael Lauk, Freiburg (DE)

(73) Assignee: respimetrix GmbH, Münster (DE)

(*) Notice: Subject to any disclaimer, the term of this patent is extended or adjusted under 35 U.S.C. 154(b) by 791 days.

(21) Appl. No.: 15/125,511

(22) PCT Filed: Mar. 10, 2015

(86) PCT No.: PCT/US2015/019711
§ 371 (c)(1),
(2) Date: Sep. 12, 2016

(87) PCT Pub. No.: WO2015/138454
PCT Pub. Date: Sep. 17, 2015

(65) Prior Publication Data
US 2017/0079557 A1 Mar. 23, 2017

Related U.S. Application Data (60) Provisional application No. 61/950,624, filed on Mar. 10, 2014.

(51) Int. Cl.
*A61M 15/00* (2006.01)
*A61B 5/087* (2006.01)
(Continued)

(52) U.S. Cl.
CPC ............ *A61B 5/087* (2013.01); *A61B 5/0002* (2013.01); *A61B 5/0878* (2013.01);
(Continued)

(58) Field of Classification Search
CPC .... A61B 2562/0219; A61B 2562/0271; A61B 5/0002; A61B 5/0816; A61B 5/082;
(Continued)

(56) References Cited

U.S. PATENT DOCUMENTS 5,363,842 A * 11/1994 Mishelevich ........ A61B 8/0875
128/200.14
5,794,612 A * 8/1998 Wachter ............ A61M 15/0086
128/200.23
(Continued)

FOREIGN PATENT DOCUMENTS

| EP | 1037683 A1 | 9/2000 |
|---|---|---|
| EP | 1944036 A2 | 7/2008 |
| EP | 2335758 A2 | 6/2011 |

OTHER PUBLICATIONS

Lareau et al., "Improving adherence with inhaler therapy in COPD," Int. J. Chron. Obstruct. Pulmon. Dis. 2010; 5: pp. 401-406.

*Primary Examiner* — Annette Dixon
(74) *Attorney, Agent, or Firm* — Venable LLP; Henry J. Daley (57) ABSTRACT

A system for delivering an agent to be taken up by a user's lungs and for simultaneously monitoring the user's lung health includes an inhalant-flow detection system and a computer-executable medium. The inhalant-flow detection system includes a flow sensor arranged to intercept a portion of inhalant flowing through the system and to provide detection signals regarding inhalant speed as a function of time. The computer-executable medium includes non-transient computer code, which when executed on a computer, causes the computer to receive the detection signals from the flow sensor, receive information about a quantity and type of agent provided by the agent delivery device for the inhalant during the inhalation time period, and calculate a delivered dose of the agent based on at least the detection signals (Continued)

received, the information received about the quantity and type of agent, and information concerning physiology of the user.

23 Claims, 4 Drawing Sheets

(51) Int. Cl.
*A61B 5/00* (2006.01)
*A61M 16/00* (2006.01)

(52) U.S. Cl.
CPC .............. *A61B 5/7282* (2013.01); *A61B 5/74* (2013.01); *A61M 15/009* (2013.01); *A61M 15/0021* (2014.02); *A61M 15/0065* (2013.01); *A61M 15/0086* (2013.01); *A61B 2560/0209* (2013.01); *A61B 2560/0214* (2013.01); *A61B 2562/028* (2013.01); *A61M 2016/0036* (2013.01); *A61M 2205/3334* (2013.01); *A61M 2205/3561* (2013.01); *A61M 2205/3576* (2013.01); *A61M 2205/3584* (2013.01); *A61M 2205/3592* (2013.01); *A61M 2205/502* (2013.01); *A61M 2205/52* (2013.01); *A61M 2205/6018* (2013.01); *A61M 2205/6054* (2013.01); *A61M 2205/6072* (2013.01); *A61M 2205/8206* (2013.01); *A61M 2205/8212* (2013.01)

(58) Field of Classification Search
CPC ....... A61B 5/083; A61B 5/087; A61B 5/1117; A61B 5/4839; A61B 5/681; A61B 5/6831; A61B 8/0875; A61J 7/0418; A61J 7/0436; A61J 7/0463; A61J 7/0481; A61M 11/003; A61M 11/005; A61M 11/006; A61M 11/007; A61M 11/041; A61M 11/042; A61M 11/08; A61M 15/00; A61M 15/0005; A61M 15/0016; A61M 15/0018; A61M 15/002; A61M 15/0021; A61M 15/0065; A61M 15/008; A61M 15/0083; A61M 15/0085; A61M 15/0086; A61M 15/0088; A61M 15/009; A61M 16/0003; A61M 16/104; A61M 16/109; A61M 16/18; A61M 2016/0021; A61M 2016/0024; A61M 2016/0027; A61M 2016/003; A61M 2016/0039; A61M 2016/0042; A61M 2205/13; A61M 2205/14; A61M 2205/276; A61M 2205/3306; A61M 2205/332; A61M 2205/3334; A61M 2205/3368; A61M 2205/3375; A61M 2205/35; A61M 2205/3553; A61M 2205/3561; A61M 2205/43; A61M 2205/44; A61M 2205/50; A61M 2205/502; A61M 2205/52; A61M 2205/581; A61M 2205/582; A61M 2205/583; A61M 2205/82; A61M 2205/8206; A61M 2206/10
See application file for complete search history.

(56) References Cited

U.S. PATENT DOCUMENTS

| | | | |
|---|---|---|---|
| 6,958,691 B1* | 10/2005 | Anderson | A61B 5/0002 340/539.12 |
| 9,555,202 B2* | 1/2017 | Von Hollen | A61M 15/009 |
| 2004/0016427 A1* | 1/2004 | Byron | A61M 11/041 128/200.14 |
| 2005/0087189 A1 | 4/2005 | Crockford et al. | |
| 2005/0172958 A1 | 8/2005 | Singer et al. | |
| 2010/0089394 A1* | 4/2010 | Sakurada | A61B 5/087 128/203.14 |
| 2010/0282245 A1* | 11/2010 | Star | G01N 27/4146 128/200.14 |
| 2012/0285447 A1* | 11/2012 | Schipper | A61B 5/1117 128/200.16 |
| 2012/0291779 A1* | 11/2012 | Haartsen | A61M 15/0065 128/203.12 |
| 2013/0008436 A1* | 1/2013 | Von Hollen | A61M 15/0086 128/200.14 |
| 2013/0092158 A1 | 4/2013 | Levy et al. | |
| 2013/0186392 A1 | 7/2013 | Haartsen et al. | |
| 2014/0034051 A1 | 2/2014 | Addington et al. | |

* cited by examiner

SYSTEMS AND METHODS FOR DELIVERING AN AGENT TO A USER'S LUNGS AND FOR SIMULTANEOUSLY MONITORING LUNG HEALTH

CROSS-REFERENCE OF RELATED APPLICATION

This application claims priority to U.S. Provisional Application No. 61/950,624, filed Mar. 10, 2014, the entire contents of which are hereby incorporated by reference.

BACKGROUND

1. Technical Field

The field of the currently claimed embodiments of this invention relates to systems and methods for delivering an agent to be taken up by a user's lungs and for simultaneously monitoring the user's lung health.

2. Discussion of Related Art

Numerous chronic respiratory diseases, for example asthma, chronic obstructive pulmonary disease and cystic fibrosis, are treated with devices that release a controlled dose of medication to the patient's lungs. There are two prominent device classes today, the so-called metered dose inhalers (MDI), where the activation by the patient triggers an aerosol dose driven by a propellant, or the dry powder inhalers, where the patient is actively inhaling a fine powder substance driven by his/her breathing airflow.

The two most prominent diseases treated with MDIs are asthma and chronic obstructive pulmonary disease (COPD). While the clinical effectiveness of the therapies is well documented, major problems arise because of the degree of the patients' adherence to the therapy. There are different types of non-adherence: "erratic", "unwitting", and "intelligent".

The "erratic" type typically either forgets to use the inhalers on a regular basis, or the inhalation process itself is performed in a wrong way, either because the operation of the releasing mechanism is not synchronized with inhaling, or because the inhalation is not strong enough, or, the opposite, too strong and not lasting long enough. In fact the recommended flow range is within a narrow range that the patient barely can judge from instructions such as "breathe deeply" or alike.

The "unwitting" adherence type is characterized by a lack of education; for example, patients do not understand how often they should use the medication, when, and how, and also why.

The last group, called the "intelligent" non-adherent patient, is intentionally not taking the medication, for example, because the patient thinks he does not need the treatment.

All types of non-adherent patients use an amount of inhaled medication that deviates from the prescribed dosage or prescribed usage procedure.

All different non-adherence types can be addressed by feedbacks, education, support, and monitoring (see, for example, Int. J. Chron. Obstruct. Pulmon. Dis. 2010; 5: 401-406).

In addition to problems concerning the above mentioned therapy adherence, it is desired that the patients regularly perform breathing test maneuvers, for example a forced expiration maneuver, or peak flow measurements to assess the health status of the lung.

It is key for a successful treatment to motivate patients and engage them using their medications on a regular basis. A device has to be extremely simple to use, not bothersome, portable, easy to clean, and preferably adding features that the patients like to use to also address the unwitting and intelligent types of non-adherence. In addition, given the large number of patients suffering from chronic respiratory disease, it is basic that the device has a reasonably low manufacturing price while still delivering clinically accurate data. U.S. Pat. No. 5,363,842 describes a device with an integrated flow sensor and a movement sensor to record the device usage and the inhalation process itself. A small LCD screen provides feedback to the patient. U.S. Pat. No. 5,505,195 discloses a device that can be used to measure flow in a dry powder inhaler using a thermistor as slow sensor. However, the prior art fails to accurately determine the amount of an inhalant that reaches the user's lungs and does not automatically monitor lung health. Therefore, there remains a need for improved systems and methods for delivering an agent to be taken up by a user's lungs and for simultaneously monitoring the user's lung health.

SUMMARY

A system for delivering an agent to be taken up by a user's lungs and for simultaneously monitoring said user's lung health according to an embodiment of the current invention includes an inhalant-flow detection system and a computer-executable medium. The inhalant-flow detection system includes a tube having a first end to receive air intake and a second end having a shape and size suitable to be used as a mouth piece for a user to receive inhalant therethrough. The first end is one of attached to or configured to be attachable to an agent delivery device. The agent delivery device is configured to supply a quantified dose of the agent into air flowing through the tube to provide the inhalant. The inhalant-flow detection system includes a flow sensor arranged to intercept a portion of inhalant flowing through the tube and to provide detection signals regarding inhalant speed as a function of time. The computer-executable medium includes non-transient computer code, which when executed on a computer, causes the computer to receive the detection signals from the flow sensor for an inhalation time period of the agent, receive information about a quantity and type of agent provided by the agent delivery device for the inhalant during the inhalation time period, calculate a delivered dose of the agent to be taken up by the user's lungs based on at least the detection signals received, the information received about the quantity and type of agent, and information concerning physiology of the user, and provide an output signal based on the delivered dose calculated. Also, the inhalant-flow detection system is configured to provide substantially non-turbulent, unobstructed air flow from the first end to the second end of the tube.

A method for quantifying delivery of an agent to be taken up by a user's lungs and for simultaneously monitoring the user's lung health using a computer according to an embodiment of the current invention includes receiving, by the computer, inhalant-flow signals from an inhalant-flow detection system for an inhalant over an inhalation time period; receiving, by the computer, information about a quantity and type of agent contained within the inhalant during the inhalation time period; calculating, using the computer, a delivered dose of the agent to be taken up by the user's lungs based on at least the inhalant-flow signals received, the information received about the quantity and type of agent, and information concerning physiology of the user; and providing an output signal, from the computer, based on the delivered dose calculated.

A computer-executable medium according to an embodiment of the current invention includes non-transient computer code for quantifying delivery of an agent to be taken up by a user's lungs and for simultaneously monitoring the user's lung health, which when executed on a computer, causes the computer to receive inhalant-flow signals from an inhalant-flow detection system for an inhalant over an inhalation time period; receive information about a quantity and type of agent contained within the inhalant during the inhalation time period; calculate a delivered dose of the agent to be taken up by the user's lungs based on at least the inhalant-flow signals received, the information received about the quantity and type of agent, and information concerning physiology of the user; and provide an output signal based on the delivered dose calculated.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Accordingly, an embodiment of the current invention provides a device that can be attached to an inhaler (MDI or powder or mist). For example, an embodiment can be structured to be attached to, but not limited to, existing metered dose inhalers, dry powder inhalers, and/or nebulizers. The device can include a low resistance airflow sensing tube having a reduced cross-sectional area, an upstream tube opening and a downstream tube opening positioned in the air passage, and an electronic module sensing the differential pressure using a MEMS element, and wirelessly submitting the measured data to a smartphone, tablet, or other computing device.

Another aspect of some embodiments of the current invention is that the same device can be used as a personal spirometer if not attached to a MDI; patients can perform, on a regular basis, physiological measurements of breathing as Forced expiration or Peak flow.

Another aspect of some embodiments of the current invention is that the device can provide a highly dynamical flow signal that can be assessed between 100 and more than 1000 times per second, for example, and that can be used to derive an individual biomarker that represents lung health status, and that can be calculated from the inhalation flow trace so that the user does not have to perform a separate maneuver.

Another aspect of some embodiments of the current invention is that the inhaled dose and pharmacokinetics can be estimated based on the dynamics of the flow curve and the volume calculated. This can enable, for example, an adjustment the user's individual inhalation schedule based on the actual drug intake.

According to some embodiments, the device can be extremely simple to use. The measurements can be started and stopped automatically. The device can be low cost to manufacture since it does not process the data and does not require any user interaction. In some embodiments, a coupled smartphone or tablet can be used as a processing and gateway unit and can provide many additional features, including patient motivation programs, online data sharing, educational and real-time feedback training programs to improve the inhalation process and life style, e-commerce options, tracking, and communication with doctors and caregivers.

Some embodiments of the current invention can provide the following features:

a) Provide a direct measure of the ingestion of the drug, not only if the device mechanism has been released (e.g., pressed).

b) Using directly the breathing airflow is the only non-invasive way to do that; however, the dynamics of the flow sensor is a critical point: to capture onset and shape of the flow curve a very fast response is required; thermistors and classical spirometer technologies are too slow. Such measurements can provide a number of new possibilities:

i) Calculate a biomarker for lung health from the high-dynamic inhalation profile.

ii) Dynamic airflow and inspired volume dynamics specific to inhaled drug to determine the total drug dose. The inspired fraction in peripheral vs the amount deposited in the conducting airways can be determined.

iii) Sensor can report pharmacokinetics, where drug is deposited, and bio-equivalence of inspired pharmaceutical.

iv) Based on the physical connection to the pharmaceutical device, the specific device can be identified (e.g. by an RFID chip on the device side, or a specific geometry of the connector), and an appropriate algorithm for determining medication and dose (iii) and ii) above) can be determined.

v) Can be used to measure the amount of inhaled nanostructured lipid nanocarriers used to transport pharmaceuticals, chemotherapeutics, genetic or biological agents.

vi) Can be used to determine the site of deposition (lung periphery or conducting airway) of inhaled nano-structured lipid nanocarriers used to transport pharmaceuticals, chemotherapeutics, genetic or biological agents.

c) Sensor has to be resistant to Powder particles, nanocarriers and humidity d) Device can be used with metered dose inhalers and powder inhalers
e) Device can be easily cleaned by flushing with water
f) Device does not add significant airflow restriction
g) Measurement device is inhaler device independent, i.e. can be used with different devices as an attachment to the device without integrating it in the housing (although it can be integrated)
h) Small enough to carry together with the device in your pocket without need of a special carry case, or even wall power
i) Low manufacturing price The term "airflow" is intended to have a broad definition such that it can include any gas that a user inhales during use. It can include, but is not limited to, air having a composition of the local environment, air from a local environment modified by the addition and/or removal of components, a supplied gas which can be a mixed or substantially pure gas, such as, but not limited to, oxygen, or any combination thereof.

The term "inhalant" is intended to have a broad definition to include anything that a user can or will inhale. For example, the term inhalant can refer to air as it exists in a local environment of the user, air modified from how it exists in the local environment of the user, a gas or mixture of gases, and/or any of the preceding that also contains particles suspended therein that can be inhaled by a user. For example, the term "inhalant" is intended to include, but is not limited to, air alone and air with fine particles suspended therein. The term "particles" is intended to include solid and/or liquid particles. The term "inhalant" can include, but is not limited to, air in a local environment, pure and/or mixed gas compositions such as, but not limited to, oxygen, aerosols, vapors and any combination thereof.

The term "computer" is intended to have a broad meaning to include any device, whether localized or distributed over a network that has one or more data processors, such as, but not limited to one or more CPU's (central processing units). The term "computer" can include, but is not limited to, one or more smart phones, one or more smart watches, one or more wearable computational devices, one or more tablet computers, one or more laptop computers, one or more desktop computers, or more workstation computers, and any combination thereof. The term computer can include, but is not limited to, any combination of the above-noted devices networked together in a local area network (LAN), a wide area network (WAN) and/or over the internet, for example.

The phrase "substantially non-turbulent, unobstructed air flow" means that the degree of obstruction and turbulence introduced by the inhalant-flow detection system is sufficiently small so as not to interfere with use of the system for delivering an agent to be taken up by a user's lungs.

Figure 1:
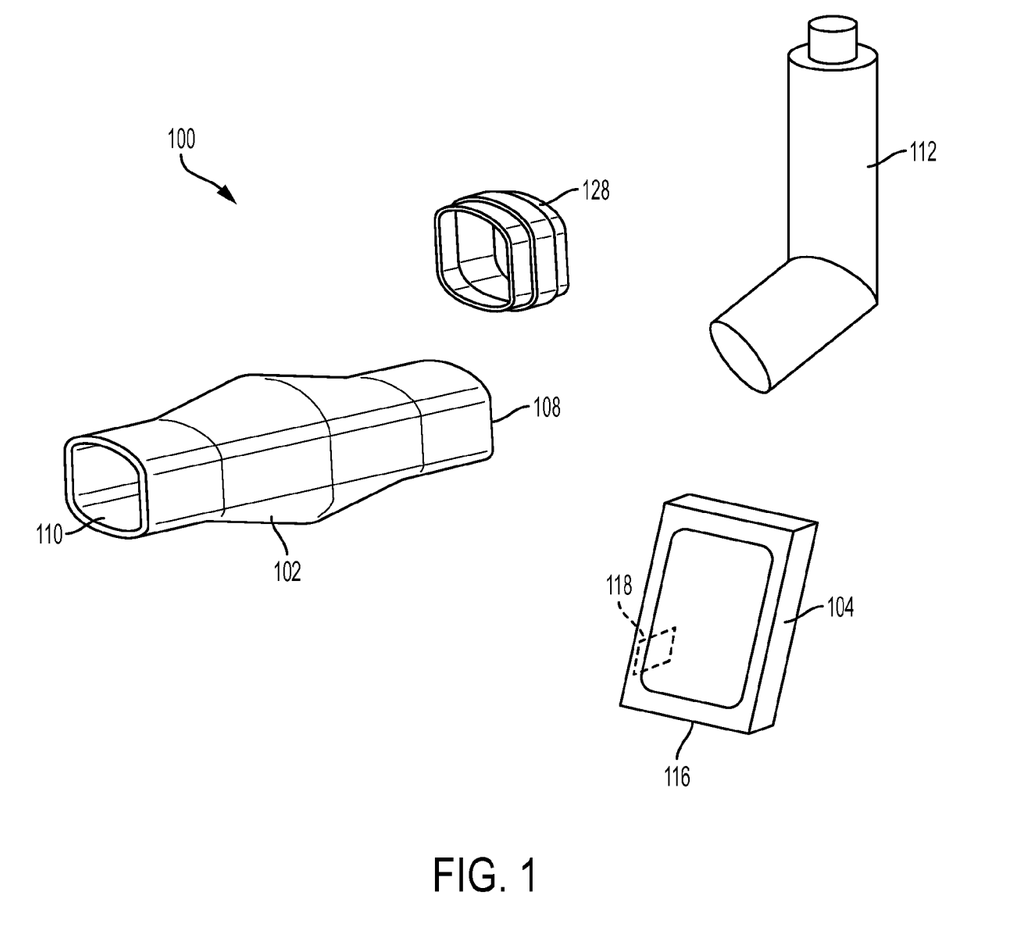
FIG. 1 is a schematic illustration of a system for delivering an agent to be taken up by a user's lungs and for simultaneously monitoring said user's lung health according to an embodiment of the current invention.

FIG. 1 is a schematic illustration of a system 100 for delivering an agent to be taken up by a user's lungs and for simultaneously monitoring said user's lung health according to an embodiment of the current invention. The system 100 includes an inhalant-flow detection system 102 and a computer-executable medium 104 comprising non-transient computer code.

Figure 2:
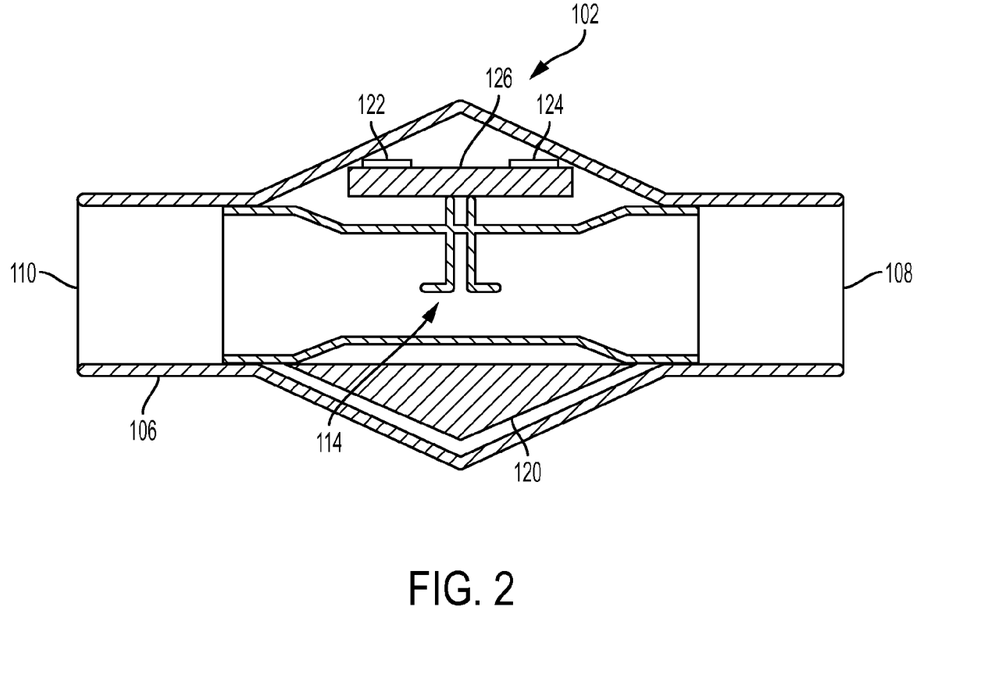
FIG. 2 is a cross-sectional view of the inhalant-flow detection system according to an embodiment of the current invention.

As illustrated in more detail in FIG. 2, the inhalant-flow detection system 102 includes a tube 106 having a first end 108 to receive air intake and a second end 110 having a shape and size suitable to be used as a mouth piece for a user to receive inhalant therethrough. The first end 108 is one of attached to or configured to be attachable to an agent delivery device 112. The agent delivery device 112 is configured to supply a quantified dose of the agent into air flowing through the tube 106 to provide the inhalant. The inhalant-flow detection system 102 also includes a flow sensor 114 arranged to intercept a portion of inhalant flowing through the tube 106 and to provide detection signals regarding inhalant speed as a function of time.

The computer-executable medium 104 can be contained at least partially on a computer 116, as is illustrated schematically as a smart phone in the embodiment of FIG. 1. However, the general concepts of the current invention are not limited to only smart phones. The computer-executable medium 104 includes non-transient computer code, which when executed on the computer 116, causes the computer 116 to:
- receive the detection signals from the flow sensor 114 for an inhalation time period of the agent,
- receive information about a quantity and type of agent provided by the agent delivery device 112 for the inhalant during the inhalation time period,
- calculate a delivered dose of the agent to be taken up by the user's lungs based on at least the detection signals received, the information received about the quantity and type of agent, and information concerning physiology of the user, and
- provide an output signal based on the delivered dose calculated.

The inhalant-flow detection system 102 is configured to provide substantially non-turbulent, unobstructed air flow from the first end 108 to the second end 110 of the tube 106.

In some embodiments, the computer-executable medium 104 can further include non-transient computer code, which when executed on the computer 116, causes the computer 116 to:
- calculate a parameter based on the detection signals received during the inhalation time period from the flow sensor 114,
- compare the parameter to at least one of a corresponding previously determined parameter from the user, a theoretically expected value of the parameter, or an empirically determined baseline value of the parameter,
- determine whether the parameter is indicative of normal lung health or indicative of abnormal lung health of the user during the inhalation time period, and
- output a signal containing information of normal lung health or abnormal lung health determined for the inhalation time period.

In some embodiments, the computer-executable medium 104 can further include non-transient computer code, which when executed on the computer 116, causes the computer 116 to send the calculated parameter to data storage device 118 to be available for later retrieval. The data storage device 118 can be on the computer 116 and/or on other external devices.

In some embodiments, the computer-executable medium 104 can further include non-transient computer code, which when executed on the computer 116, causes the computer 116 to retrieve a plurality of previously saved values of the calculated parameter and calculate at least one of a personal baseline value for the user or a time-dependent personal trend in the parameter for the user.

In some embodiments, the agent can be at least one of a therapeutic agent, a diagnostic agent, or a nutritional agent.

In some embodiments, the agent can be at least one of a bronchodilator, a long-acting beta2-agonist, an anticholinergic, a sympathomimetic, a corticosteroid, an antihistamine; insulin, a structured lipid nanocarrier as a carrier for chemotherapy.

In some embodiments, the agent can be at least one of aclidinium, ipratropium bromide, tiotropium, albuterol, arformoterol, formoterol, indacaterol, levalbuterol, metaproterenol, pirbuterol, salmeterol, beclomethasone, budesonide, ciclesonide, flunisolide, fluticasone, and mometasone.

In some embodiments, the inhalant-flow detection system 102 can further include a battery 120 configured to provide self-contained operation of the inhalant-flow detection system, a second data storage device 122 configured to save the detection signals for later retrieval, and a wireless transmitter 124 configured to transmit the signals to the computer 116. The MID-Thermic Flow Sensor produced by 2E Mechatronic has been found to be suitable for some applications. However, the general concepts of the current invention are not limited to only that particular example.

In some embodiments, the flow sensor 114 can include a flow-through microelectromechanical systems (MEMS) device 126. The flow-through MEMS device 126 can have channels with a width of at least 100 μm and less than 400 μm to prevent clogging by particles in the inhalant.

In some embodiments, the system 100 can also include computer 116 which contains the computer-executable medium 104.

In some embodiments, the system 100 can also include an adapter 128 configured to connect the tube 106 to the agent delivery device 112. In some embodiments, the system 100 can also include the agent delivery device 112 at least one of connected to or integral with the tube 106.

In some embodiments, the inhalant-flow detection system 102 can have a sleep mode and an active measuring mode such that the sleep mode uses less electrical power than said active measuring mode. In some embodiments, the inhalant-flow detection system 102 can further have a usage interrogation mode that periodically checks status of usage of the inhalant-flow detection system and automatically switches the inhalant-flow detection system from sleep mode to active measuring mode based on a result of an interrogation.

Figure 3:
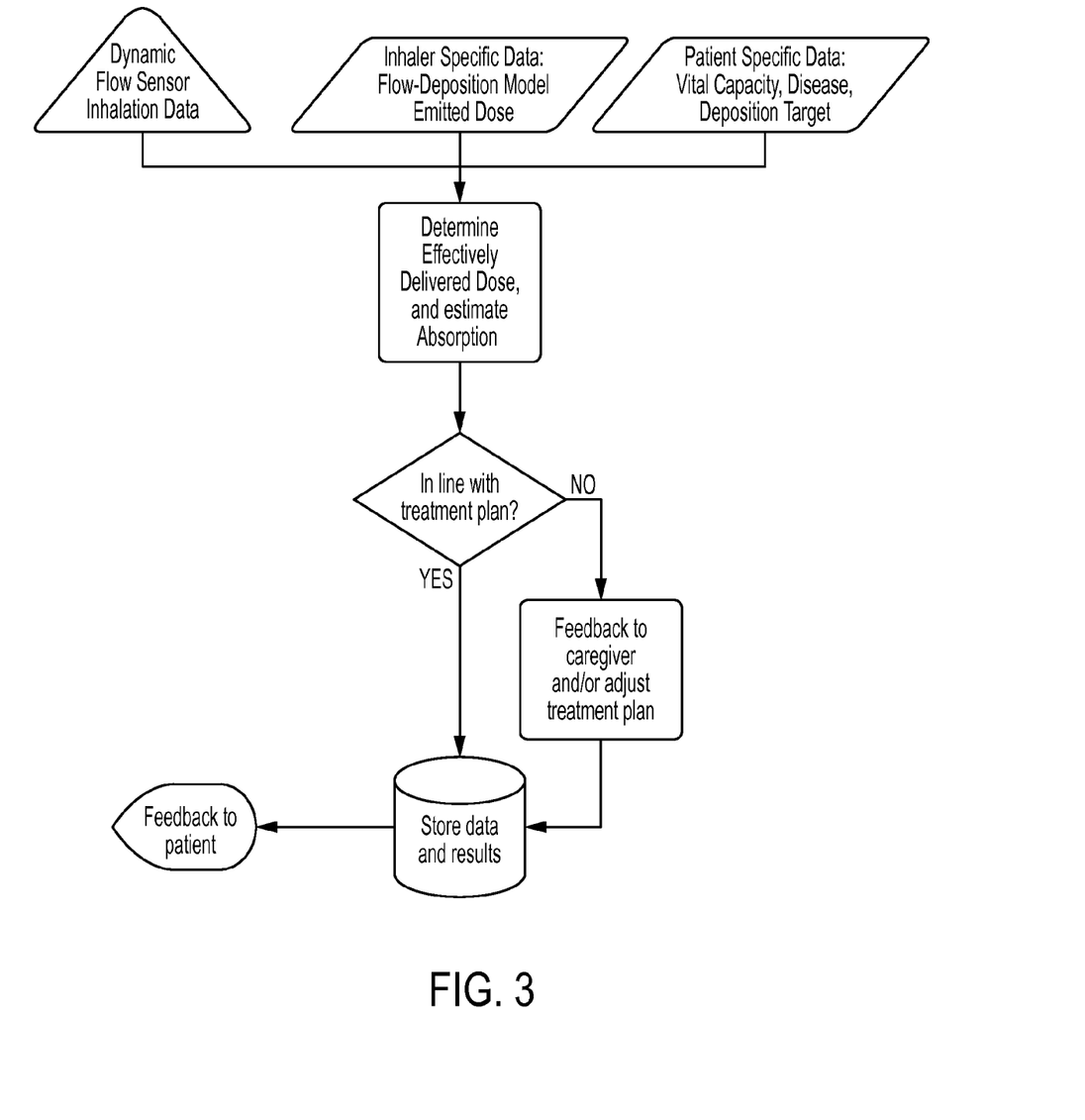
FIG. 3 is a flow chart illustrating agent dose determination according to an embodiment of the current invention.
Figure 4:
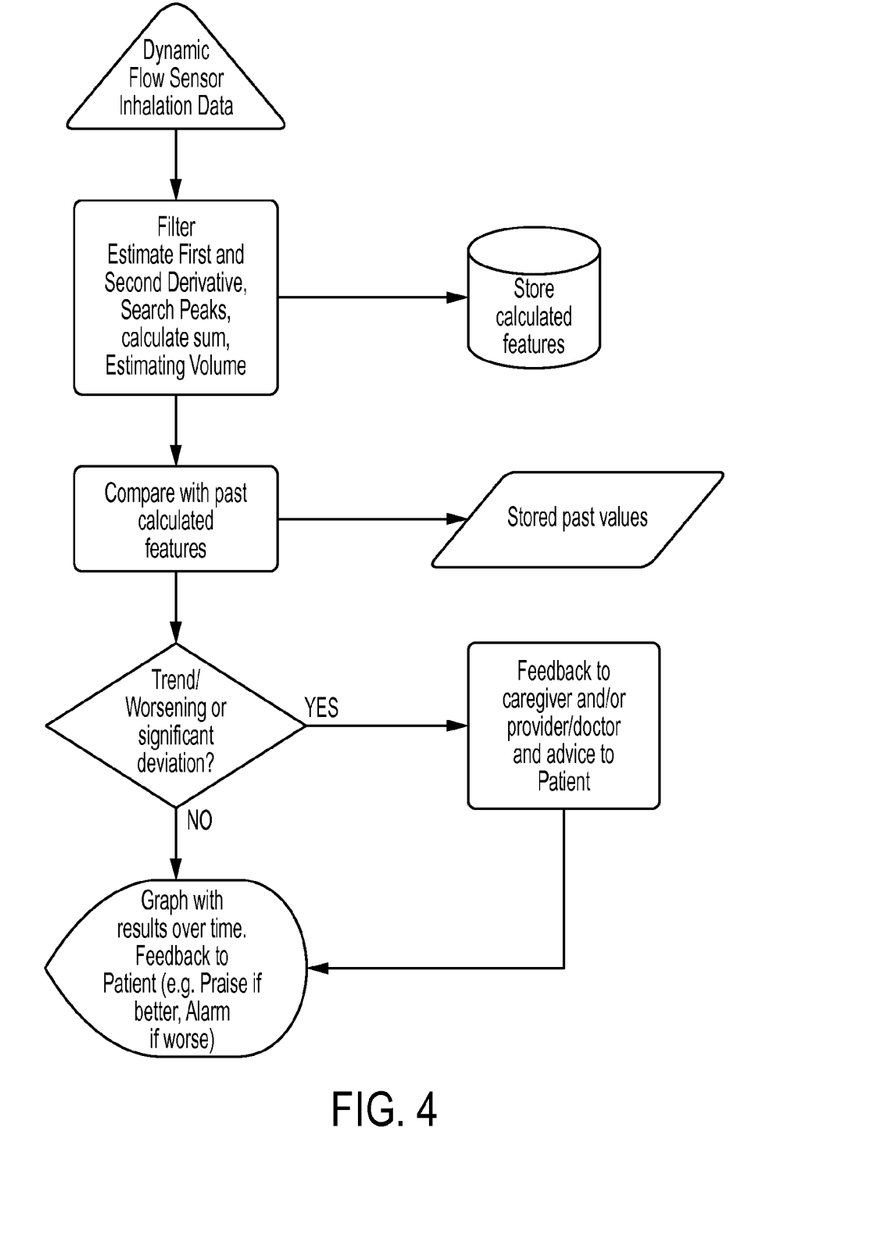
FIG. 4 is a flow chart illustrating lung health assessment according to an embodiment of the current invention.

FIGS. 3 and 4 help explain the operation of the system 100 for dose calculation and monitoring aspects, respectfully. In operation, a user uses agent delivery device 112 to provide a measured dose of the agent. The information concerning the type of agent and the quantity of the dose can be known in advance for specific devices and stored in a look-up table, for example. They could also be contained within barcodes, RFID tags, etc. that could be read into the system. However, the general concepts of the invention can include other ways of providing knowledge of the amount and type of agent provided, such as real-time measurements, for example. The user inhales the inhalant that contains the agent from the agent delivery device 112. The inhalant-flow detection system 102 measures, in real time, a flow speed profile as a function of time as the user inhales the inhalant.

Information about the user can be input and/or retrieved from storage to include in the calculations. The information can include, but is not limited to, age and health of the user, for example. It can include model information that models the amount of inhalant that reaches a user's lungs under the measured conditions, for example. The model can be a general theoretical mode, a semi-empirical model, and/or empirical model. The user input data can be static data once stored, or it could be modified and updated by previous usage of the system 100 and/or by external input.

The computer 116 then calculates the amount of the agent that reached the user's lungs for the specific dose being taken up. In some embodiments, the computer can further estimate the amount of agent absorbed by the user's lungs for the specific case. This can be performed in real time to provide feedback to the user. This can provide useful information such as indicating that a smaller dose was actually received than was intended. This can allow the user to take another dose planned to make up for the deficiency. In addition, the history of use of the device can be stored and/or sent to other parties, such as the user's caregiver.

FIG. 4 helps illustrate a lung health monitoring aspect according to some embodiments of the current invention. In conjunction with the administering of a dose of the agent as described above, the same flow data can be analyzed to calculate one or more parameters that can be indicative of normal or abnormal inhalation function. For example, the first derivative and/or second derivation of the initial increase in the flow curve can serve as a biomarker. Such a parameter can be compared to a baseline for the parameter established previously for the particular user, for example. The parameter could also be stored and/or sent to another party, such as the caregiver. There can also be an alert that can be sent, for example, if an abnormality, or certain category of abnormality is detected.

Another embodiment of the current invention includes a method for quantifying delivery of an agent to be taken up by a user's lungs and for simultaneously monitoring the user's lung health using a computer. The method includes receiving, by the computer, inhalant-flow signals from a inhalant-flow detection system for an inhalant over an inhalation time period; receiving, by the computer, information about a quantity and type of agent contained within the inhalant during the inhalation time period; calculating, using the computer, a delivered dose of the agent to be taken up by the user's lungs based on at least the inhalant-flow signals received, the information received about the quantity and type of agent, and information concerning physiology of the user; and providing an output signal, from the computer, based on the delivered dose calculated.

The method can further include calculating, by the computer, a parameter based on the inhalant-flow signals; comparing, using the computer, the parameter to at least one of a corresponding previously determined parameter from the user, a theoretically expected value of the parameter, or an empirically determined baseline value of the parameter; determining, using the computer, whether the parameter is indicative of normal lung health or indicative of abnormal lung health of the user during the inhalation time period; and outputting, from the computer, a signal containing information of normal lung health or abnormal lung health determined for the inhalation time period.

The method can further include sending, using the computer, the calculated parameter to data storage to be available for later retrieval.

The method can further include retrieving, using the computer, a plurality of previously saved values of the calculated parameter; and calculating, using the computer, at least one of a personal baseline value for the user or a time-dependent personal trend in the parameter for the user.

According to another embodiment of the current invention, a computer-executable medium includes non-transient computer code for quantifying delivery of an agent to be taken up by a user's lungs and for simultaneously monitoring the user's lung health. The non-transient computer code, when executed on a computer, causes the computer to:

receive inhalant-flow signals from an inhalant-flow detection system for an inhalant over an inhalation time period;

receive information about a quantity and type of agent contained within the inhalant during the inhalation time period;

calculate a delivered dose of the agent to be taken up by the user's lungs based on at least the inhalant-flow signals received, the information received about the quantity and type of agent, and information concerning physiology of the user; and provide an output signal based on the delivered dose calculated.

The computer-executable medium can further include non-transient computer code, which when executed on the computer, causes the computer to:

calculate a parameter based on the inhalant-flow signals;

compare the parameter to at least one of a corresponding previously determined parameter from the user, a theoretically expected value of the parameter, or an empirically determined baseline value of the parameter;

determine whether the parameter is indicative of normal lung health or indicative of abnormal lung health of the user during the inhalation time period; and output a signal containing information of normal lung health or abnormal lung health determined for the inhalation time period.

The computer-executable medium can further include non-transient computer code, which when executed on the computer, causes the computer to send the calculated parameter to data storage to be available for later retrieval.

The computer-executable medium can further include non-transient computer code, which when executed on the computer, causes the computer to:

retrieve a plurality of previously saved values of the calculated parameter; and calculate at least one of a personal baseline value for the user or a time-dependent personal trend in said parameter for said user.

The following describes some concepts and some examples in more detail. The general concepts of the current invention are not limited to the particular examples.

An embodiment of the current invention provides an apparatus that measures flow via a tube that has an air passage with reduced cross-sectional area. Such a structure can help to provide non-turbulent flow through the central region of the tube. It also has an upstream tube opening and a downstream tube opening attached to a pressure sensing electronics. The apparatus is constructed in a way that it can be fluidly connected to metered dose inhaler devices. The flow sensing tube is reduced in cross section at least at one portion of the airflow passage such that the overall flow resistance is low and so that the user's breathing is not significantly obstructed while using the device.

Within the tube, the flow is measured using a differential pressure sensor principle using an upstream and a downstream opening to accurately assess flow and pressure values over a large range of flow with a low resistance. (See, e.g., US 2008/0092898, the entire contents of which are incorporated herein by reference.)

The two upstream and downstream openings may be covered by a filter material, or a foam like material to prevent powders, particles, or aerosols from clogging the measurement openings.

In another embodiment, the sensor used includes the tube and a MEMS element measuring flow with two thermopiles, whereas the internal channels of the thermopiles are so large that powder particles that potentially enter the sensor can float through the sensor without clogging the channels. In addition, the heated thermopiles are resistant to humidity that may enter the sensor, because fluid particles would be vaporized quickly.

The flow measurement tube is a simple to manufacture and can be a low cost plastic part. In one embodiment, the device could be designed in a way that this plastic part is a replacement part. The device cleaning becomes a simple process. In another embodiment, the device electronics parts can be completely enclosed in the housing, charging (if required at all) can be performed via induction, so that the device as a whole can be rinsed with a cleaning solution or water for simple cleaning.

The tube can be designed in a way to keep the airflow through the tube laminar and avoid higher resistance or turbulences. Data from the differential pressure sensor can then be linearized, digitized and stored for further analysis or immediately transferred such as via wireless technologies, for example Bluetooth, to a Smartphone, a tablet, a Smartwatch, or similar mobile platform or a computer.

An advantage of one embodiment is that the device can be attached to the outlet of existing metered dose inhalers or powder inhalers as they are widely used today, and there is no need to redesign and integrate it in the packaging or housing of the inhaler itself. Most of them use similar shapes and sizes; some will need a specific adaptor or specific outside form factors. All other parts of the device will be the same for almost all drug inhalers currently used. It also can be used with other breathing related drug delivery devices and units, such as aerosol inhalation devices.

Alternatively, the same device can be used as a personal spirometer without an inhaler attached to it to perform breathing related measures and maneuvers such as Forced Expiration or Peak Flow measures. Key for this application is the fact the sensor as described above is bi-directional and covers a large range of flows.

One aspect of some embodiments of the invention is that we can derive from the measured, high dynamic flow curve a biomarker representative for the individual lung health status, for example, calculated by using first and second derivatives of the first portion of the inhalation curve profile, or any other affine transformation. Using this marker instead of having the patient performing a second, separate spirometer maneuver can have a major advantage since the daily routine of taking the medication delivers at the same time information about the lung health.

Another aspect is that the measured signal can be used to estimate the biological equivalent drug dose that reached the lung for a specific, individual inhalation process. For inhaled drugs, the pharmacokinetics and the drug dose that reaches the blood highly depend on how the inhalation process is performed by the patient. If the flow dynamics and volume of the inhalation process is known, it can be estimated (knowing the drug content and inhaler type) how much of the released drug dose reached the lung. This could be used to adjust and adapt the individual treatment plan and schedule.

The sensor device itself does not require any user interaction. Start and Stop can be automatically triggered by the flow crossing a threshold value, and this by the start of a measurement itself. The synchronization between the release process of the drug and the start of inhalation can be estimated solely based on the measured flow data. If required, the device could be used together with a special educational program running on the tablet or Smartphone as a training device to improve the inhalation process.

Since all processing and display can be done via Smartphone or tablets or another external computing device that is not part of the sensor, the sensor electronics can be designed to operate with low energy; the device itself does not require powerful and energy consuming processing units or a display. In addition, the manufacturing price of the device can be low since it only contains the sensing part, a means to wirelessly transmit the data, memory to store raw data, and a battery.

Due to the low manufacturing price, the sensor part may be integrated in the inhaler device itself, without massively increasing the cost of the inhaler, or selectively providing the device only for a particular target patient group (which would make the distribution process much more difficult).

One advantage in some embodiments is that the processing devices, i.e. Smartphones and tablets, are powerful computing devices that allow much more computing intensive analysis routines without increasing the price of the device itself. This can allow the device to operate with lower quality and thus lower priced sensor data and compensate, for example, for higher noise using advanced methods of time series analysis.

The advantage using a Smartphone or a tablet as a processing and gateway device is not only the manufacturing price and simplicity and computational power. Some embodiments of the current invention can also provide numerous additional services to patients, doctors, payers, and caring givers, since mobile devices are typically connected in various forms to wide area networks, thus the internet is readily accessible. Some embodiments can allow for the assessment of the frequency and quality of the inhalation and the health status of the lung using the same data, and allows one to detect if the inhalation has been performed accurately.

The attached Smartphone can provide instant or later feedback to patient or inform care givers if inhalation was not performed accurately. Some embodiments of the invention can also be used to automatically trigger the delivery of replacements if the drug container is close to empty or too old.

The device can be used as a training device with training software programs running on the Smartphone or tablet for learning how to correctly inhale (using placebo substances).

The Smartphone based device allows one to additionally provide education and motivational programs, such as integrated walk tests, tracking activity, quit smoking programs, healthy food, exercise programs, or air quality warnings that are based on location detection, that are used to engage and motivate patients.

One advantage of some embodiments of the invention is that it can provide feed-back to the patient on multiple levels:
1) Real-time during the inhalation process on the screen
2) Automatic device generated feedback: immediately after the inhalation: inhalation quality, and lung health status in comparison to historic values
3) Automatic device generated feedback: Reminders, warnings, tipps
4) Message based feedback from caregivers, after uploading the data to the internet (doctors, providers, relatives, nurses, etc.)
5) Phone based feedback in case of urgent issues
6) Long term education and training programs Another feature of some embodiments of the invention is the introduction of Group Identification numbers (GroudIDs). The GroupID allows doctors, payers, hospitals, pharmacies, and companies to access their patient group (or a sub-group of their patients) as a whole group anonymously for study purposes, and allows for the customization of the software running on the Smartphone, tablet and computers of a specific group.

In one embodiment, the patient decides actively with whom he wants to share the recorded data. The patient is identified with a code only, so that the company providing the device and services can handle all patient related data anonymously, but the medical provider can identify the patient using his data base if the patient agreed to share the data with a particular provide/doctor/hospital. The advantage of this patient centric "push" like data transmission systems is that is simplifies the fulfillment of international data security regulations.

In FIG. 1 the measurement tube and electronics are embedded in a plastic housing that has a mouthpiece on second end 110. For use as a breathing measurement device (a personal spirometer), the patient breaths through the device; the first end 108 is left open to the atmosphere. For use with an inhaler to assess quality and frequency of inhalation, the device will be attached to the inhaler device at the first end 108; there will be different adaptors to fit the opening to the different available devices.

In FIG. 2, the measurement sensing tube is embedded in the outside housing that adds space for the sensor and electronics and the battery.

Some embodiments can include a method of calculating from the dynamics of an inhalation flow profile measured during the inhalation process using a pulmonary drug delivery device pharmacokinetic parameters, such as the delivered dose, the absorbed drug content, and distribution.

The estimates of the pharmacokinetics can be based on stored values, curves, and functions for a specific inhaler device. In some embodiments, the inhaled substance can be carried by nanostructured lipid nanocarriers that can be used to transport pharmaceuticals, chemotherapeutics, genetic or biological agents, or any other nano-particle that can be delivered with the inhaled breathing airflow.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A system for delivering an agent to be taken up by a user's lungs and for simultaneously monitoring said user's lung health, comprising:

an inhalant-flow detection system, comprising:
a tube having a first end to receive air intake and a second end having a shape and size suitable to be used as a mouth piece for a user to receive inhalant therethrough, said first end being one of attached to or configured to be attachable to an agent delivery device, wherein said agent delivery device is configured to supply a quantified dose of said agent into air flowing through said tube to provide said inhalant, and
a flow sensor arranged to intercept a portion of inhalant flowing through said tube and to provide detection signals regarding inhalant speed as a function of time; and
a computer-executable medium comprising non-transient computer code, which when executed on a computer, causes the computer to:

receive said detection signals from said flow sensor for an inhalation time period of said agent, receive information about a quantity and type of agent provided by said agent delivery device for said inhalant during said inhalation time period, calculate a delivered dose of said agent to be taken up by said user's lungs based on at least said detection signals received, said information received about said quantity and type of agent, and information concerning physiology of said user, and provide an output signal based on said delivered dose calculated, wherein said inhalant-flow detection system is configured to provide substantially non-turbulent, unobstructed air flow from said first end to said second end of said tube.

2. The system of claim 1, wherein said agent is at least one of a therapeutic agent, a diagnostic agent, or a nutritional agent.

3. The system of claim 1, wherein said agent is at least one of a bronchodilator, a long-acting beta2-agonist, an anticholinergic, a sympathomimetic, a corticosteroid, an antihistamine; insulin, a structured lipid nanocarrier as a carrier for chemotherapy.

4. The system of claim 1, wherein said agent is at least one of aclidinium, ipratropium bromide, tiotropium, albuterol, arformoterol, formoterol, indacaterol, levalbuterol, metaproterenol, pirbuterol, salmeterol, beclomethasone, budesonide, ciclesonide, flunisolide, fluticasone, and mometasone.

5. The system of claim 1, further comprising the computer, said computer comprising said computer-executable medium.

6. The system of claim 1, further comprising an adapter configured to connect said tube to an agent delivery device.

7. The system of claim 1, further comprising an agent delivery device at least one of connected to or integral with said tube.

8. The system of claim 1, wherein said inhalant-flow detection system has a sleep mode and an active measuring mode, and
wherein said sleep mode uses less electrical power than said active measuring mode.

9. The system of claim 8, wherein said inhalant-flow detection system has a usage interrogation mode that periodically checks status of usage of the inhalant-flow detection system and automatically switches the inhalant-flow detection system from sleep mode to active measuring mode based on a result of an interrogation.

10. The system of claim 1, wherein said computer-executable medium further comprises non-transient computer code, which when executed on the computer, causes the computer to:
calculate a parameter based on said detection signals received during said inhalation time period from said flow sensor,
compare said parameter to at least one of a corresponding previously determined parameter from said user, a theoretically expected value of said parameter, or an empirically determined baseline value of said parameter,
determine whether said parameter is indicative of normal lung health or indicative of abnormal lung health of said user during said inhalation time period, and
output a signal containing information of normal lung health or abnormal lung health determined for said inhalation time period.

11. The system of claim 10, wherein said computer-executable medium further comprises non-transient computer code, which when executed on the computer, causes the computer to:
send said calculated parameter to data storage to be available for later retrieval.

12. The system of claim 11, wherein said computer-executable medium further comprises non-transient computer code, which when executed on the computer, causes the computer to:
retrieve a plurality of previously saved values of said calculated parameter; and
calculate at least one of a personal baseline value for said user or a time-dependent personal trend in said parameter for said user.

13. The system of claim 1, wherein said inhalant-flow detection system further comprises:
a battery configured to provide self-contained operation of said inhalant-flow detection system,
a data storage device configured to save said detection signals for later retrieval, and
a wireless transmitter configured to transmit said signals to the computer.

14. The system of claim 13, wherein said flow sensor comprises a flow-through microelectromechanical systems (MEMS) device.

15. The system of claim 14, wherein said flow-through MEMS device comprises channels with a width of at least 100 μm and less than 400 μm.

16. A method for quantifying delivery of an agent to be taken up by a user's lungs and for simultaneously monitoring said user's lung health using a computer, comprising:
receiving, by said computer, inhalant-flow signals from an inhalant-flow detection system for an inhalant over an inhalation time period;
receiving, by said computer, information about a quantity and type of agent contained within said inhalant during said inhalation time period;
calculating, using said computer, a delivered dose of said agent to be taken up by said user's lungs based on at least said inhalant-flow signals received, said information received about said quantity and type of agent, and information concerning physiology of said user; and
providing an output signal, from said computer, based on said delivered dose calculated.

17. The method of claim 16, further comprising:
calculating, by said computer, a parameter based on said inhalant-flow signals;
comparing, using said computer, said parameter to at least one of a corresponding previously determined parameter from said user, a theoretically expected value of said parameter, or an empirically determined baseline value of said parameter;
determining, using said computer, whether said parameter is indicative of normal lung health or indicative of abnormal lung health of said user during said inhalation time period; and
outputting, from said computer, a signal containing information of normal lung health or abnormal lung health determined for said inhalation time period.

18. The method of claim 17, further comprising sending, using said computer, said calculated parameter to data storage to be available for later retrieval.

19. The method of claim 18, further comprising:
retrieving, using said computer, a plurality of previously saved values of said calculated parameter; and calculating, using said computer, at least one of a personal baseline value for said user or a time-dependent personal trend in said parameter for said user.

20. A computer-executable medium comprising non-transient computer code for quantifying delivery of an agent to be taken up by a user's lungs and for simultaneously monitoring said user's lung health, which when executed on a computer, causes the computer to:
receive inhalant-flow signals from an inhalant-flow detection system for an inhalant over an inhalation time period;
receive information about a quantity and type of agent contained within said inhalant during said inhalation time period;
calculate a delivered dose of said agent to be taken up by said user's lungs based on at least said inhalant-flow signals received, said information received about said quantity and type of agent, and information concerning physiology of said user; and
provide an output signal based on said delivered dose calculated.

21. The computer-executable medium of claim 20, further comprising non-transient computer code, which when executed on the computer, causes the computer to:
calculate a parameter based on said inhalant-flow signals;
compare said parameter to at least one of a corresponding previously determined parameter from said user, a theoretically expected value of said parameter, or an empirically determined baseline value of said parameter;
determine whether said parameter is indicative of normal lung health or indicative of abnormal lung health of said user during said inhalation time period; and
output a signal containing information of normal lung health or abnormal lung health determined for said inhalation time period.

22. The computer-executable medium of claim 21, further comprising non-transient computer code, which when executed on the computer, causes the computer to send said calculated parameter to data storage to be available for later retrieval.

23. The computer-executable medium of claim 22, further comprising non-transient computer code, which when executed on the computer, causes the computer to:
retrieve a plurality of previously saved values of said calculated parameter; and
calculate at least one of a personal baseline value for said user or a time-dependent personal trend in said parameter for said user.

* * * * *